US009549833B2

(12) United States Patent
McHugo

(10) Patent No.: US 9,549,833 B2
(45) Date of Patent: Jan. 24, 2017

(54) STENT DELIVERY, REPOSITIONING, AND REMOVAL SYSTEM

(71) Applicant: Cook Medical Technologies LLC, Bloomington, IN (US)

(72) Inventor: Vincent McHugo, Co. Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 623 days.

(21) Appl. No.: 13/648,591

(22) Filed: Oct. 10, 2012

(65) Prior Publication Data

US 2013/0090714 A1 Apr. 11, 2013

Related U.S. Application Data

(60) Provisional application No. 61/545,755, filed on Oct. 11, 2011.

(51) Int. Cl.
| | | |
|---|---|---|
| *A61F 2/06* | (2013.01) | |
| *A61F 2/95* | (2013.01) | |
| *A61F 2/90* | (2013.01) | |
| *A61F 2/07* | (2013.01) | |

(52) U.S. Cl.
CPC . *A61F 2/95* (2013.01); *A61F 2/90* (2013.01); *A61F 2002/075* (2013.01); *A61F 2002/9511* (2013.01); *A61F 2002/9528* (2013.01); *A61F 2002/9534* (2013.01); *A61F 2220/0008* (2013.01); *A61F 2220/0075* (2013.01); *A61F 2230/0078* (2013.01)

(58) Field of Classification Search
CPC ........ A61F 2/07; A61F 2/95; A61F 2002/075; A61F 2/89; A61F 2002/9511
USPC ... 623/1.11, 1.12, 1.13, 1.15, 1.18, 1.2, 1.22
See application file for complete search history.

(56) References Cited

U.S. PATENT DOCUMENTS

| | | | | |
|---|---|---|---|---|
| 2003/0040771 A1* | 2/2003 | Hyodoh | ................... | A61F 2/90 606/200 |
| 2004/0116996 A1* | 6/2004 | Freitag | ..................... | A61F 2/88 623/1.11 |
| 2008/0140181 A1* | 6/2008 | Reynolds | .................. | A61F 2/91 623/1.15 |
| 2008/0243225 A1* | 10/2008 | Satasiya | ................... | A61F 2/91 623/1.12 |

(Continued)

FOREIGN PATENT DOCUMENTS

| | | |
|---|---|---|
| JP | 2010-511429 | 4/2010 |
| WO | WO 2006/047520 A2 | 5/2006 |

(Continued)

OTHER PUBLICATIONS

Notification of Transmittal of the International Search Report and the Written Opinion of the International Searching Authority, or the Declaration, dated Nov. 28, 2012, for corresponding application PCT/US2012/059444, 5p.

*Primary Examiner* — Tuan V Nguyen
*Assistant Examiner* — Kevin Everage
(74) *Attorney, Agent, or Firm* — Brinks Gilson & Lione

(57) ABSTRACT

A system for the delivery, repositioning, and removal of a stent is provided that utilizes inherent properties of stents, such as wire woven helical stents, including foreshortening. The stent can be radially constrained to reduce its diameter by applying a tensile force along its proximal and distal ends to collapse the stent permitting the delivery, repositioning, and removal of the stent.

15 Claims, 6 Drawing Sheets

(56) References Cited

U.S. PATENT DOCUMENTS

2009/0204199 A1 8/2009 Jensen et al.
2011/0190865 A1 8/2011 McHugo et al.

FOREIGN PATENT DOCUMENTS

| WO | WO 2008/066923 A1 | 6/2008 |
| WO | WO 2009/102435 A1 | 8/2009 |
| WO | WO 2011/094527 A1 | 8/2011 |

* cited by examiner

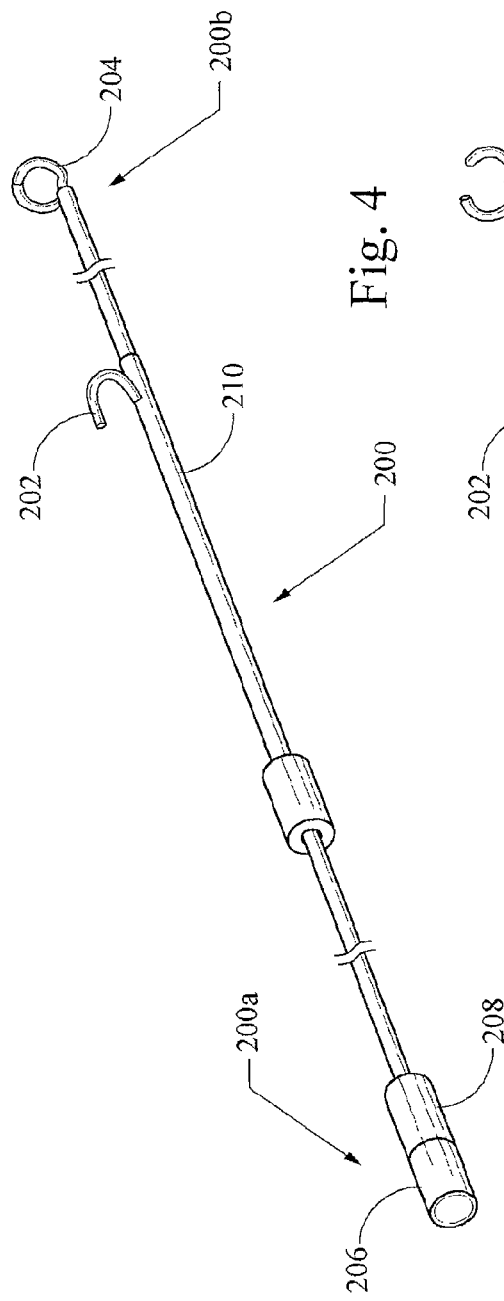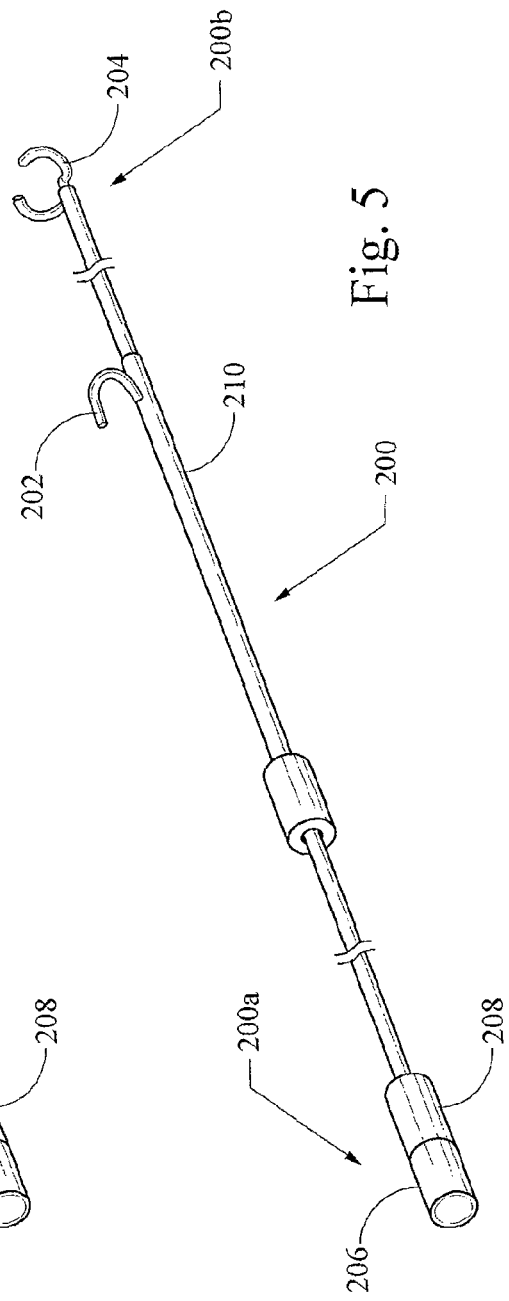

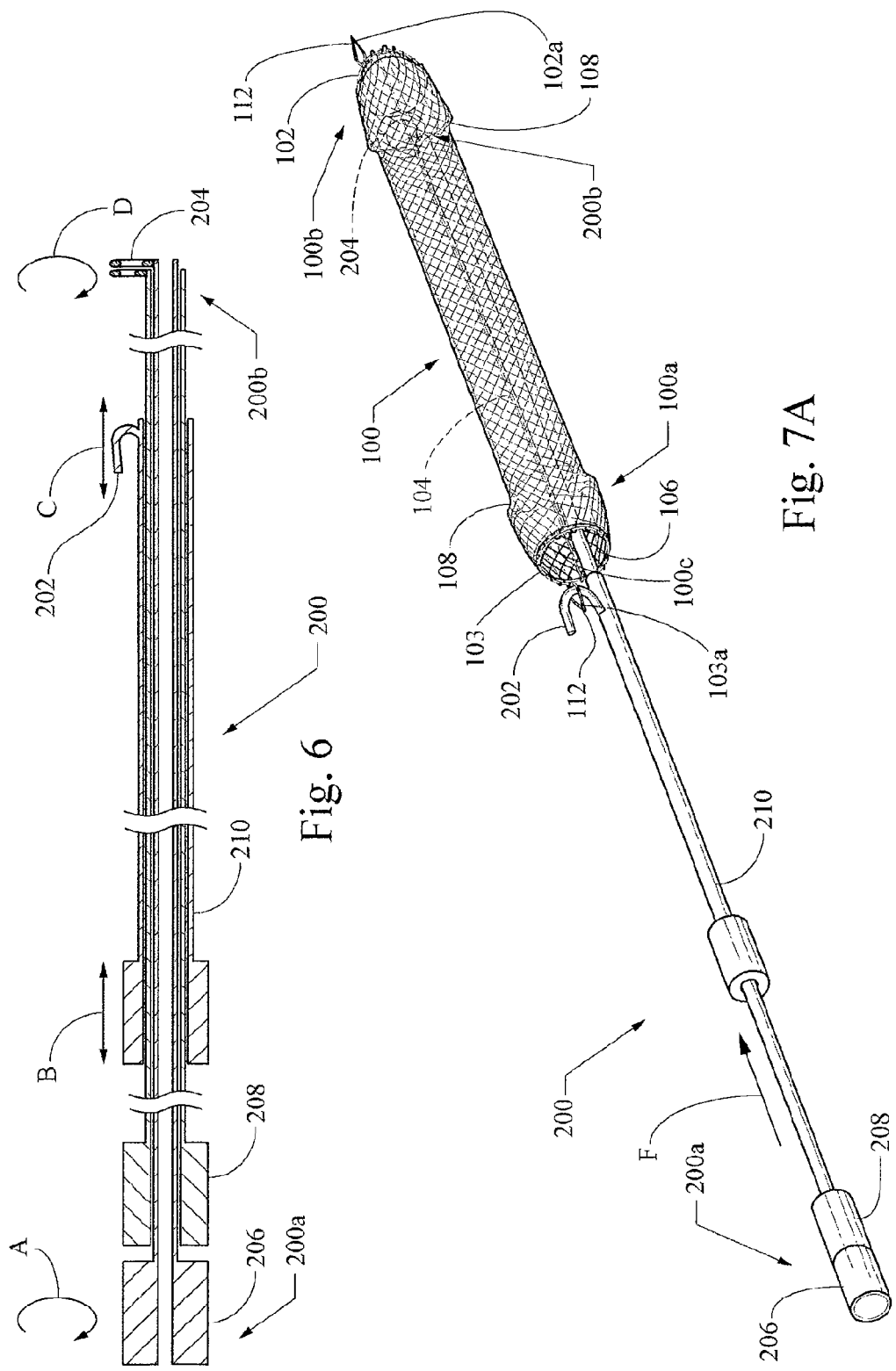

STENT DELIVERY, REPOSITIONING, AND REMOVAL SYSTEM

RELATED APPLICATION

This application claims the benefit of priority from U.S. Provisional Application No. 61/545,755, filed Oct. 11, 2011, and titled "Stent Delivery, Repositioning, and Removal System", the contents of which is incorporated herein by reference.

TECHNICAL FIELD

The present invention relates to medical devices and more specifically, stents.

BACKGROUND

Self expanding stents are useful for a variety of procedures requiring the maintenance of the patency of a bodily pathway. Such stents are generally biased to expand, such that when deployed, they assume an open position, pushing outward and into the surrounding area into which deployed. The radial expansion creates or maintains a pathway in a once occluded or weak area.

Avoiding the use of a traditional sheath for deploying a stent, such as a self-expanding stent, is desired to avoid many of the shortcomings resulting from sheath deployment. For example, the sheath release delivery devices are difficult to reposition or remove and slow to operate. The stent may only be partially-deployed prior to reconstrainment of the stent by the sheath in order to still reposition or remove the stent. Once the stent is fully deployed, i.e. radially expanded, the sheath cannot reconstrain the stent to allow it to be repositioned or removed. For example, utilizing a conventional outer sheath/inner catheter delivery device may cause the physician to inadvertently use excessive force and pull back the outer sheath too far, thereby prematurely deploying the stent in an incorrect position within a bodily lumen. At this step in the procedure, repositioning of the stent becomes difficult, if not impossible, because the stent has already radially self-expanded into the bodily lumen. Additionally, retraction of the outer sheath in a controlled manner is often difficult which may lead to uneven or inadvertent jerking back of the outer sheath and improper positioning of the stent.

Moreover, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the proximal portion of the stent may elongate or foreshorten while still covered by the outer sheath or after the sheath releases the stent. Foreshortening is a property inherent in some self expanding stents. It is the property describing the characteristic of a stent that when in an expanded state it generally has a length shorter than when in a collapsed state. Foreshortening may result in a stent being deployed in the wrong position because the stent shortens during expansion, such as when after being deployed.

The positioning of the stent body in the central portion of the target region may also be difficult with a distal stent release system. An additional drawback occurs with the sheathed stent delivery system where direct visualization of the stent is required. For example, with endoscopically placed stents, the sheath tends to prevent or obscure the location of the stent, making accurate placement of the stent more difficult. Accurate placement of the proximal portion of the stent and/or the stent body may be important in certain applications, for example to prevent stent migration or to properly open a stricture along the entire length of the stricture.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed (or collapsed) within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysterics in the movement of the stent. The sheathed stent delivery device also requires more space within an endoscope compared to a sheathless device and also adds additional expense to the delivery system.

BRIEF SUMMARY

In a first aspect, a stent is provided having an elongated tubular body having a proximal portion, a distal portion, and a lumen extending between the proximal portion and distal portion, wherein the elongated tubular body has one or more wires; a first suture connected circumferentially to the proximal portion of the elongated tubular body, wherein the first suture is configured into a first grasping loop; a second suture connected circumferentially to the distal portion of the elongated tubular body; a third suture at least partially disposed within the lumen of the elongated tubular body, wherein the third suture is connected to the first suture and the second suture; wherein the stent is configured to collapse and assume a collapsed diameter when opposite axial forces are applied to the first grasping loop and the third suture.

In a second aspect, a positioning device for use with a stent is provided having a proximal portion; a distal portion; a shaft; a hook disposed on an outer surface of the shaft; an actuation member configurable into an open position and a closed position; an actuator in communication with the actuation member, wherein the actuator is configured to open and close the actuation member; an advancement/retraction member in communication with the actuator and the actuation member, wherein the advancement/retraction member is slideably disposed within at least a portion of the shaft, wherein the advancement/retraction member is configured to axially move the actuation member in a direction proximally toward and distally from the hook.

In a third aspect, a stent positioning system is provided having a stent including: an elongated tubular body including a proximal portion, a distal portion, and a lumen extending between the proximal portion and the distal portion; a first suture connected to the proximal portion of the elongated tubular body, wherein the first suture is configured into a first grasping loop; a second suture connected to the distal portion of the elongated tubular body; and a third suture at least partially disposed within the lumen of the elongated tubular body, wherein the third suture is connected to the first suture and the second suture; a positioning device including: a proximal portion; a distal portion; a shaft; a hook disposed on an outer surface of the shaft and configured to engage the first grasping loop of the stent; an actuation member configurable into an open position and a closed position, wherein the actuation member is configured to engage the third suture of the stent; an actuator in communication with the actuation member, wherein the actuator is configured to open and close the actuation member; an advancement/retraction member in communication with the actuator and the actuation member, wherein the advancement/retraction member is slideably disposed within at least a portion of the shaft, wherein the advancement/retraction member is configured to axially move the actuation member in a direction proximally toward and distally from the hook; wherein, the stent is configured to collapse and assume a collapsed diameter when the actuation member is engaged with the third suture, wherein the hook is engaged with the first grasping loop, and further wherein the advancement/retraction member is directed axially such that the actuation member is moved distally from the hook.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

FIG. 4 illustrates a perspective view of an exemplary stent positioning device wherein the actuation member is closed;

FIG. 5 illustrates a perspective view of the exemplary stent positioning device illustrated in FIG. 4, wherein the actuation member is open;

FIG. 6 illustrates a sectional side view of the exemplary stent positioning device illustrated in FIG. 4;

FIGS. 7A-7B illustrate the exemplary stent positioning device illustrated in FIG. 4 in use.

DETAILED DESCRIPTION OF PRESENTLY PREFERRED EMBODIMENTS

Figure 1:
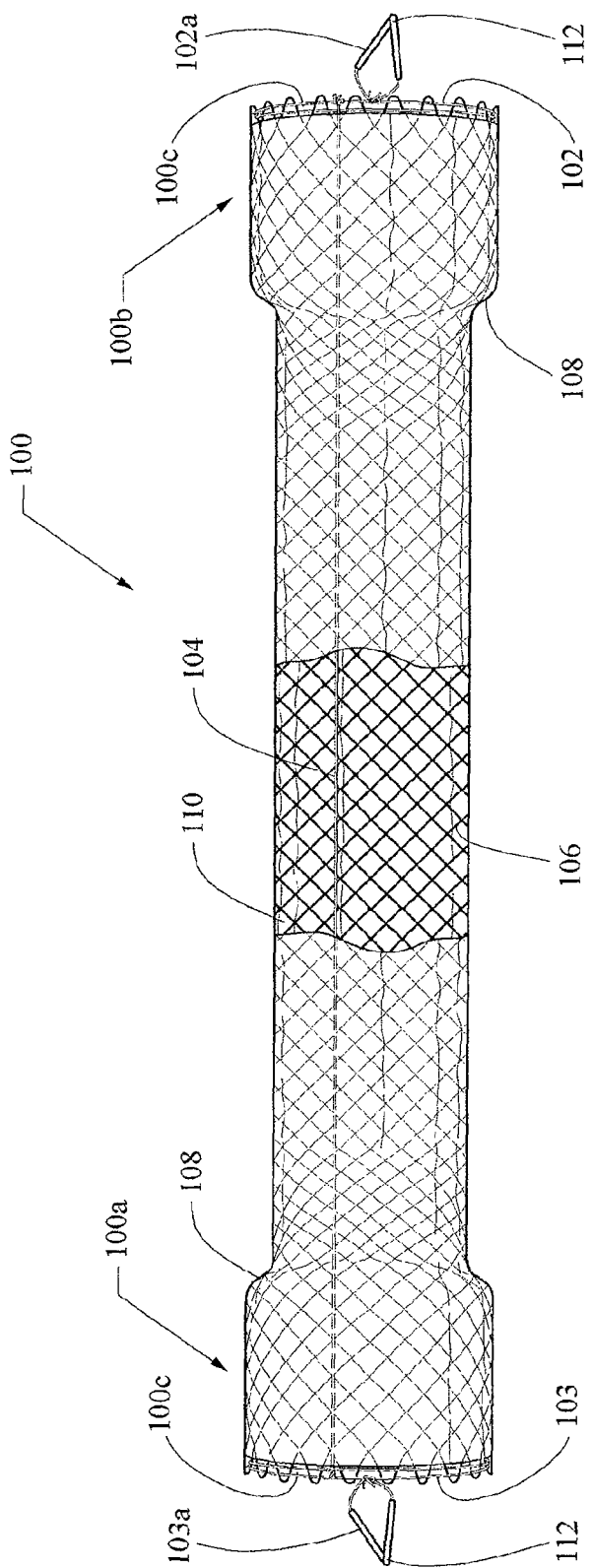
FIG. 1 illustrates a partial sectional side view of an exemplary modified stent for use with a stent positioning device.

The exemplary embodiments illustrated herein provide exemplary apparatuses for delivering, repositioning, and removing a stent. The present invention is not limited to those embodiments described herein, but rather, the disclosure includes all equivalents and those intended to be included in the claims. For example, the principles herein can be applied to other types of stents, including but not limited to, self expanding metal stents, self expanding laser cut peripheral artery stents, woven wire stents, and the EVOLUTION® (Wilson-Cook Medical Inc.).

Moreover, the embodiments illustrated herein can be used in any portion of the body benefiting from an indwelling medical device, such as a stent, that is able to be repositioned or removed after partial or full deployment, including but not limited to, the gastrointestinal region, esophageal region, duodenum region, biliary region, colonic region, as well as any other bodily region or field, and they are not limited to the sizes, shapes, or configurations illustrated herein.

Unless otherwise defined, all technical and scientific terms used herein have the same meaning as commonly understood by one of ordinary skill in the art. In case of conflict, the present document, including definitions, will control. Preferred methods and materials are described below, although apparatuses, methods, and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

The term "patient," as used herein, is not limited to being a human being; animals and others are contemplated. User is contemplated throughout the disclosure as being anyone or thing capable of using the device, including but not limited to, a human being and machine.

A more detailed description of the embodiments will now be given with reference to FIGS. 1-8. Throughout the disclosure, like reference numerals and letters refer to like elements. The present disclosure is not limited to the embodiments illustrated; to the contrary, the present disclosure specifically contemplates other embodiments not illustrated but intended to be included in the claims.

It has been discovered that the delivery, repositioning, and removal of a stent, such as a wire woven stent having a helical pitch, including but not limited to an esophageal stent, can be improved through a system that uses the inherent properties of such a stent, including foreshortening. From the discovery of the system, the stent can be radially constrained to reduce its diameter by applying a tensile force along its proximal and distal ends to collapse the stent permitting the delivery, repositioning, and removal of the stent.

Figure 2:
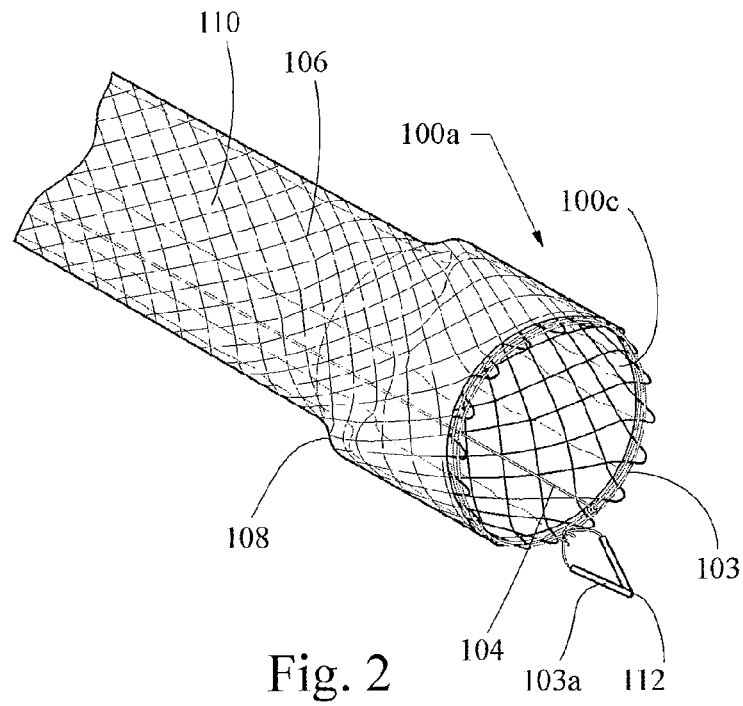
FIG. 2 illustrates a perspective front view of an exemplary modified stent for use with a stent positioning device.

FIG. 1 illustrates a partial sectional side view of exemplary modified stent 100 for use with a stent positioning device, such as that illustrated in FIG. 4 and further discussed below. FIG. 2 illustrates a perspective front view of proximal portion 100a of stent 100 illustrated in FIG. 1.

Referring to FIGS. 1-2, stent 100 is an elongated generally tubular body having proximal portion 100a, distal portion 100b, and lumen 100c extending between proximal portion 100a and distal portion 100b. The tubular body is generally constructed from one or more filaments or wires 106 that may be of various cross-sectional shapes and sizes. For example, wires 106 may be flat in shape or may have a circular-shaped cross-section. Wires 106 may have any suitable diameter, such as, for example, from about 0.10 to about 0.30 mm.

As will be described in greater detail below, expandable stents illustrated and equivalents thereto may be formed from a variety of biocompatible materials. Wires 106 preferably comprise one or more elastically deformable materials such as shape memory alloys (e.g., stainless steel, nitinol, and the like), although other materials are contemplated. Wires 106 may also be made from or comprise any suitable biocompatible material(s). For example, stents illustrated and equivalents thereto may include materials such as stainless steel, nitinol, MP35N, gold, tantalum, platinum or platinum iridium, niobium, tungsten, Iconel® (available from Special Metals Corporation, Huntington, W. Va.), ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Stents illustrated and equivalents thereto may be fabricated to any suitable dimensions. Stents illustrated and equivalents thereto having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

Stents illustrated and equivalents thereto may include a central body portion and one or more uniform flanges, or it may have two asymmetrically shaped flanges. A stent may include a uniform diameter along the length of stent but include slightly flared 108 proximal end 100a and/or distal end 100b of the stent. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the proximal and distal ends engage healthy tissue adjacent the diseased area. Although stent 100 is depicted as having a substantially uniform diameter on the longitudinal axis and flares (or flanges) 108 having a slightly larger diameter than the middle portion, other stent configurations are possible.

Stents illustrated and equivalents thereto may have any suitable helical pattern or angle such as those illustrated in FIGS. 1-3, as further discussed below. The radial force of the stent may be controlled by adjusting the angle accordingly. Stents with higher angles typically exert greater radial force and exhibit greater foreshortening during expansion from a compressed state. Stents with lower angles typically exert lower radial force and experience less foreshortening upon expansion. In some instances, the angle can be lowered because the membrane covering typically adds rigidity to the stent structure. In addition to adjusting the angle, the radial force of the stent can be adjusted through selection of particular filament materials, as well as the shape and size of the filaments or wires forming the stent structure.

Stents illustrated and equivalents thereto may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of wires 106. In some embodiments, a stent may include four radiopaque markers with two markers affixed to a first flange and two to a second flange. Optionally, radiopacity can be added to a stent through covering (also referred to as coating) processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

Stents illustrated and equivalents thereto may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract.

Although covering 110 is illustrated as being a silicone elastomer, which is desired given its ability to stretch generally 500-700% without being compromised and such, is useful in stent applications, other covering materials are contemplated, including but not limited to, polyethane (the fibers of which could be applied in layers at the same pitch of wires 106 to help close the gaps and provide a seal-like covering (but an air or water-tight seal need not be achieved)), TYVEK® (DuPont) (or other like materials) which are contemplated as being disposed between wires 106, as well as other materials such as polyurethane and non-woven materials. Indeed it is also completed that other fabric layers with filaments running in one direction that matches the pitch of one or more of stent wires 106 could be used as a covering. As such, the covering could be made up of several layers with the filaments running in one direction with a pitch similar to one or more of wires 106 with the direction of the helical pattern alternated between layers. It is contemplated that such fabric layer may be bonded to one or more of wires 106.

Indeed, in some embodiments, the covering membrane may cover over the entire stent framework from the proximal end to the distal end. In other embodiments, the stent may have a covering over a central portion of the structure and one or more uncovered ends or flanges. Moreover, a membrane covering may comprise any suitable biocompatible material. Preferably, the membrane covering is an elastic or flexible material that can adapt to radial compression of a stent prior to delivery, as well as foreshortening of a stent during expansion from a compressed state. Suitable membrane materials include, for example, as discussed above, silicones (e.g. polysiloxanes and substituted polysiloxanes), polyurethanes, thermoplastic elastomers, polyolefin elastomers, polyethylene, polytetrafluoroethylene, nylon, and combinations thereof. In some embodiments, where the stent will be implanted at or near an acidic environment (e.g., being exposed to gastric fluids), preferably the membrane covering is resistant to acid degradation.

Stents illustrated and equivalents thereto may include a membrane covering applied by any suitable method as is known in the art. For example, the membrane may be applied by spraying, dipping, painting, brushing, or padding. Generally, the membrane covering has a thickness ranging from about 0.0025 mm to about 2.5 mm. The thickness of the membrane may be selected, for example, by controlling the number of dips or passes made during the application process.

In some embodiments, a stent may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent. In such configuration, the release of the bioactive agent may be dependent on factors including composition, structure, and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a stent having multiple coverings. Different bioactive agents may be present in the different layers.

A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition, or any other method known.

Prior to applying a membrane covering, and/or a bioactive agent, a stent may be polished, cleaned, and/or primed as is known in the art. A stent may be polished, for example, with an abrasive or by electropolishing. A stent may be cleaned by inserting the stent into various solvents, degreasers, and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure.

Still referring to FIGS. 1-2, suture 102 having optional grasping loop 102a is positioned at distal portion 100b of stent 100. Suture 102 preferably comprises two thread-like elements circumferentially connected to distal portion 100b of stent 100 by being interwoven through the absolute end cells of stent 100, although other configurations are contemplated.

Suture 103 having grasping loop 103a is positioned at proximal portion 100a of stent 100. Suture 103 preferably comprises two thread-like elements circumferentially connected to proximal portion 100a of stent 100 by being interwoven through the absolute end cells of stent 100, although other configurations are contemplated.

An additional suture 104 is positioned longitudinally through the elongated tubular body of stent 100 and is connected to suture 103 and suture 102. Sutures 102, 103, and 104 are positioned and sized so that they do not interfere with the flow of material, such as food, bile, or blood, through stent 100.

Sutures 102, 103, and 104 facilitate with the delivery, repositioning, and removal of stent 100 during or after implantation. Sutures 102, 103, and 104 are configured to compress and collapse the stent when opposite axial force are applied to them, and more particularly when opposite axial forces are applied to suture 103 and suture 104. When one or more of the opposite axial forces are released, the stent will expand (or partially-expand (or deploy) if a force is still partially applied) thereby having a diameter larger than when in a collapsed (or partially-collapsed) diameter state.

Sutures 102, 103, and 104 are one or more thread-like members that may comprise any appropriate biocompatible material, such as for example, suture materials or other polymeric or metallic materials such as polyethylene, ultra-high molecular weight polyethylene, polyester, nylon, stainless steel, nitinol, or the like. Optionally, sutures 102, 103, and 104 may be covered with a material 112, such as suture grasping loops 102a and 103a illustrate, including but not limited to, polytetrafluoroethylene (PTFE), to prevent inadvertent cutting of the suture with a medical device, for example, forceps.

Preferably, grasping loop 103a of suture 103 is positioned proximal to proximal portion 100a of stent 100, as illustrated in FIGS. 1-2. Preferably, when the diameter-to-length-to-foreshortening ratios of stent 100 are ideal, grasping loop 103a is pulled inside stent 100 as stent 100 collapses and foreshortens. Accordingly, the ability of stent 100 to fully collapse is not impaired by sutures 102, 103, and 104.

Other suture configurations and techniques are contemplated, including but not limited to, those discussed in U.S. patent application Ser. No. 13/016,421, filed Jan. 28, 2011, entitled "Collapsing Structure for Reducing the Diameter of a Stent," and assigned to Cook Medical Technologies LLC, the entirety of which is hereby incorporated by reference.

Figure 3:
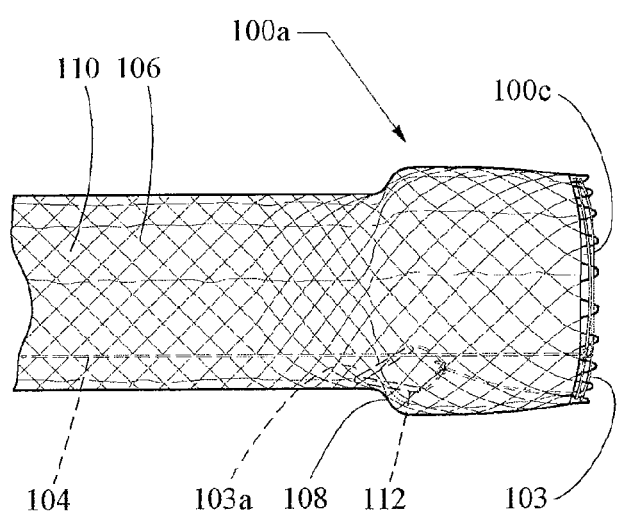
FIG. 3 illustrates an alternate side view of an exemplary modified stent for use with a stent positioning device.

FIG. 3 illustrates an alternate side view of stent 100 illustrated in FIGS. 1-2. If the diameter-to-length-to-foreshortening ratios of the stent are not ideal, suture 104 may need to be longer to accommodate the complete foreshortening of the stent. Thus, excess suture material may gather inside the inner lumen of the stent, as illustrated in FIG. 3. The additional material can be addressed, such that it does not impede collapsing or expansion of the stent, by fashioning suture from an elastic material, including but not limited to a suture comprising an elastic portion and an in-elastic material portion, such that it is configured to recoil in a controlled matter, including but not limited to, forming the in-elastic portion into a braided portion. Other materials and configurations are contemplated, including those that will stretch to a known length and then become rigid once the known length is achieved. Such a configuration permits suture 104 to be positioned beside the inner wall of the stent so as not to impact the flow of food, bile, or blood, through the stent. Other suturing techniques are contemplated.

Stents illustrated and equivalents thereto may be delivered to a body lumen using various techniques, including by use of the devices illustrated in FIGS. 4-8 and equivalents thereof.

FIGS. 4 and 5 illustrate perspective views of exemplary stent positioning device 200. FIG. 6 illustrates a sectional side view of positioning device 200.

Referring to FIGS. 4-6, positioning device 200 has two elements 204, 202 that engage respectively with suture 104 and suture grasping loop 103a of stent 100, such as that illustrated in FIGS. 1-3. Positioning device 200 includes proximal portion 200a and distal portion 200b. Hook 202 is disposed about the outer surface of shaft 210. Hook 202 engages with grasping loop 103a of exemplary stent 100.

Actuation member 204 engages suture 104 of stent 100. Actuation member 204 is connected to advancement/retraction member 208. Actuation member 204 can assume a closed position (as illustrated in FIG. 4) and an open position (as illustrated in FIG. 5) (or a partially-open or partially-closed position) by rotating actuator 206 in the direction of Arrow A, thereby causing the grasping elements of actuation member 204 to separate in the direction of Arrow D (as illustrated in FIG. 6).

Advancement/retraction member 208 is configured for axial movement through shaft 210 such that when advancement/retraction member 208 is advanced in a proximal direction or retracted in a distal direction of Arrow B, actuation member 204 moves proximally or distally, too, in the directions of Arrow C (as illustrated in FIG. 6).

Figure 7B:
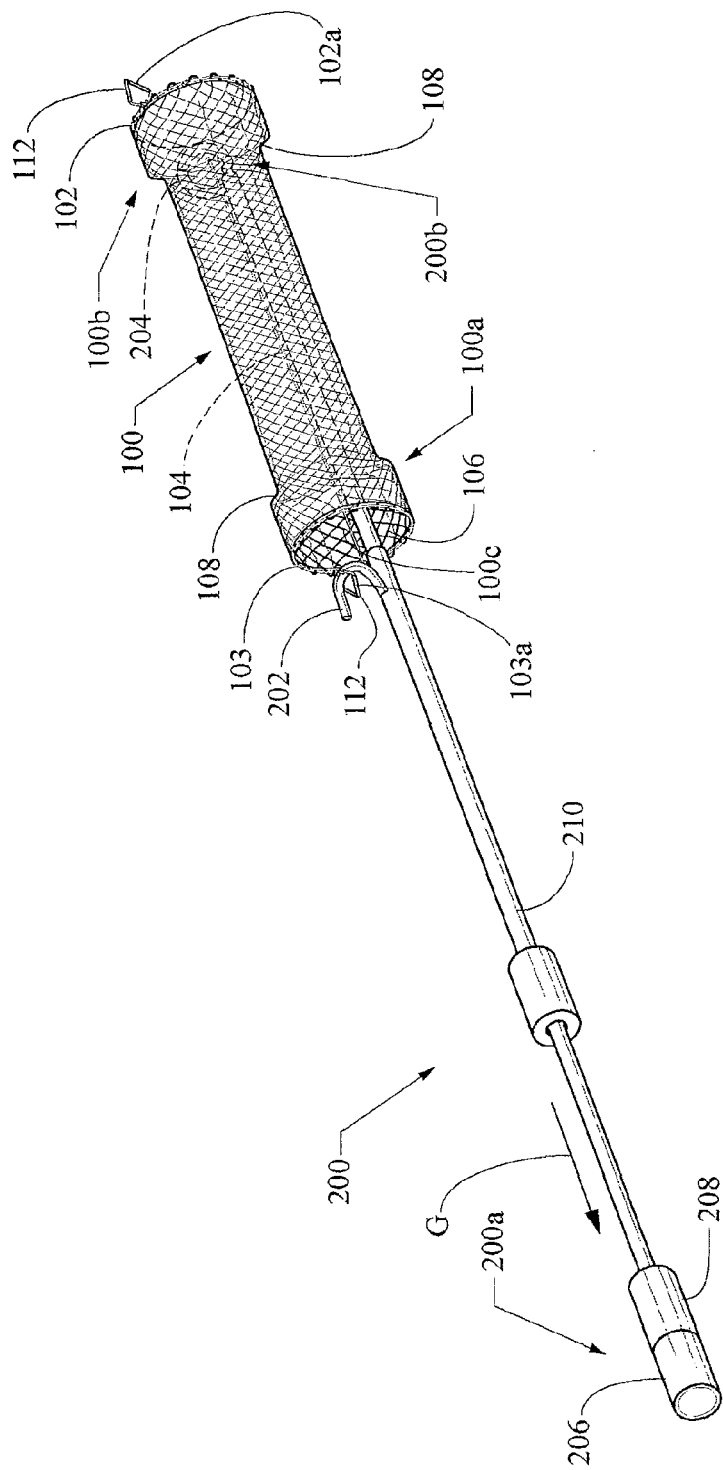

FIGS. 7A-7B illustrate positioning device 200 illustrated in FIG. 4 in use. Referring to FIG. 7A, a stent, such as that illustrated in FIG. 1, is connected to positioning device 200 such that hook 202 engages grasping loop 103a to prevent stent 100 from moving away from positioning device 200, and actuation member 204 engages suture 104 to radially compress stent. It is contemplated that hook 202 may be configured with a feature, such as a bump, angle, or other slip-prevention means, to prevent grasping loop 103a from unintentionally disengaging from hook 202.

Advancement/retraction member 208 is pushed distally in the direction of arrow F such that advancement/retraction member 208 slides distally within shaft 210 causing actuation member 204 to move in a distal direction. Accordingly, stent 100 is stretched and caused to assume a collapsed position having a diameter less than its diameter when in a fully or partially-expanded state. More specifically, collapsing of stent 100 occurs because as advancement/retraction member 208 is slid distally along suture 104, suture 104 eventually becomes taut as additional forces are applied to it as hook 202 and actuation member 204 become further separated. The force is applied equally (and opposite) to distal portion 100b and proximal portion 100a of stent because suture 104 is connected to suture 102 and suture 103 which are thereby connected to distal portion 100b and proximal portion 100a of stent. Accordingly, when suture 104 is pulled taut by actuation member 208 when directed distally, stent 100 collapses radially. Stent 100 can then be introduced into the patient. Or, alternatively, if already within the patient, stent can be repositioned or removed.

FIG. 7B illustrates a stent, such as that illustrated in FIG. 1, being deployed. Stent 100 is connected to positioning device 200 such that hook 202 engages grasping loop 103a to prevent stent 100 from moving away from positioning device 200, and actuation member 204 engages suture 104. Advancement/retraction member 208 is pulled proximally in the direction of Arrow G such that advancement/retraction member 208 slides proximally within shaft 210 causing actuation member 204 to move in a proximal direction along suture 104 thereby releasing the force exerted thereto such that suture 204 is no longer taut thereby allowing stent 100 to assume an expanded position.

Alternatively, stent 100 can be partially-collapsed or partially-expanded into any number of positions by only partially advancing or retracting advancement/retraction member 208 such that actuation member 204 varies how taut is suture 104.

Positioning device 200 and equivalents thereof provide for initial stent engagement with positioning device 200 only on proximal portion 100a of stent 100 if desired. Engagement with stent can be accomplished under endoscope view having positioning device 200 alongside the endoscope or positioning device 200 being introduced through a working channel of an endoscope. Moreover because hook 202 and actuation member 204 are first positioned close to each other (having advancement/retraction member 208 pulled distally in the direction of Arrow G (as illustrated in FIG. 7B), stent 100 can be engaged while positioning device 200 is positioned on the side proximal to stent 100. Accordingly, there is no need to initially pass positioning device 200 through lumen 100c of stent 100 to engage suture 104.

Positioning device 200 is made from PEEK, nylon, and, or stainless steel, although other materials are contemplated. The column strength of actuation member 204 is configured such that it delivers enough force to collapse a stent. For example, when configured for use with an esophageal stent, the force is about 20-40 newtons, although other forces are contemplated depending upon the configuration of stent 100.

Positioning device 200 is configured such that when advancement/retraction member 208 is pulled in its proximal-most position, hook 202 and actuation member 204 are configured such that stent is in an expanded position. For example, when configured for use with an esophageal stent, hook 202 and actuation member 204 are about 0-15 cm apart for a fully expanded state, although other distances are contemplated depending upon the configuration of stent 100. Alternatively, advancement/retraction member 208 may be retracted incrementally so as to assume any number of partially-expanded states.

When advancement/retraction member 208 is pushed in its distal-most position, hook 202 and actuation member 204 are configured such that stent is in a collapsed position. For example, when configured for use with an esophageal stent, hook 202 and actuation member 204 are about 20-40 cm apart for a fully collapsed state, although other distances are contemplated depending upon the configuration of stent 100.

Alternatively, advancement/retraction member 208 may be advanced incrementally so as to assume any number of partially-collapsed states.

Generally, under the aid of endoscopic and/or fluoroscopic visualization, positioning device 200 engaged with stent 100 may be advanced into the vicinity of the target anatomy. The targeted lumen may be predilated with a balloon catheter or other dilation device, if necessary or desired. Preferably, stent 100 is delivered in a collapsed state, such that advancement/retraction member 208 is pushed in distally in the direction of Arrow F, illustrated in FIG. 7A, thereby compressing stent 100. This approach may reduce the risk of tissue perforations during delivery.

Once stent 100 is in place, stent 100 may be released from positioning device 200 by rotating actuator 206 to open and disengage actuation member 204 from suture 104 and unhooking hook 202 from grasping loop 103*a*. If stent 100 needs to be repositioned, positioning device 200 can be reengaged with stent 100, and stent 100 can be collapsed using positioning device 200. Accordingly, stent 100 may be repositioned and removed without damaging the surrounding tissue or bodily structures because it is able to reassume a collapsed or partially-collapsed position after full or partial-deployment. Moreover, after stent 100 has been dwelling within a patient, positioning device 200 can be used to reposition or remove stent 100 without damaging the surrounding tissue or bodily structures.

Figure 8:
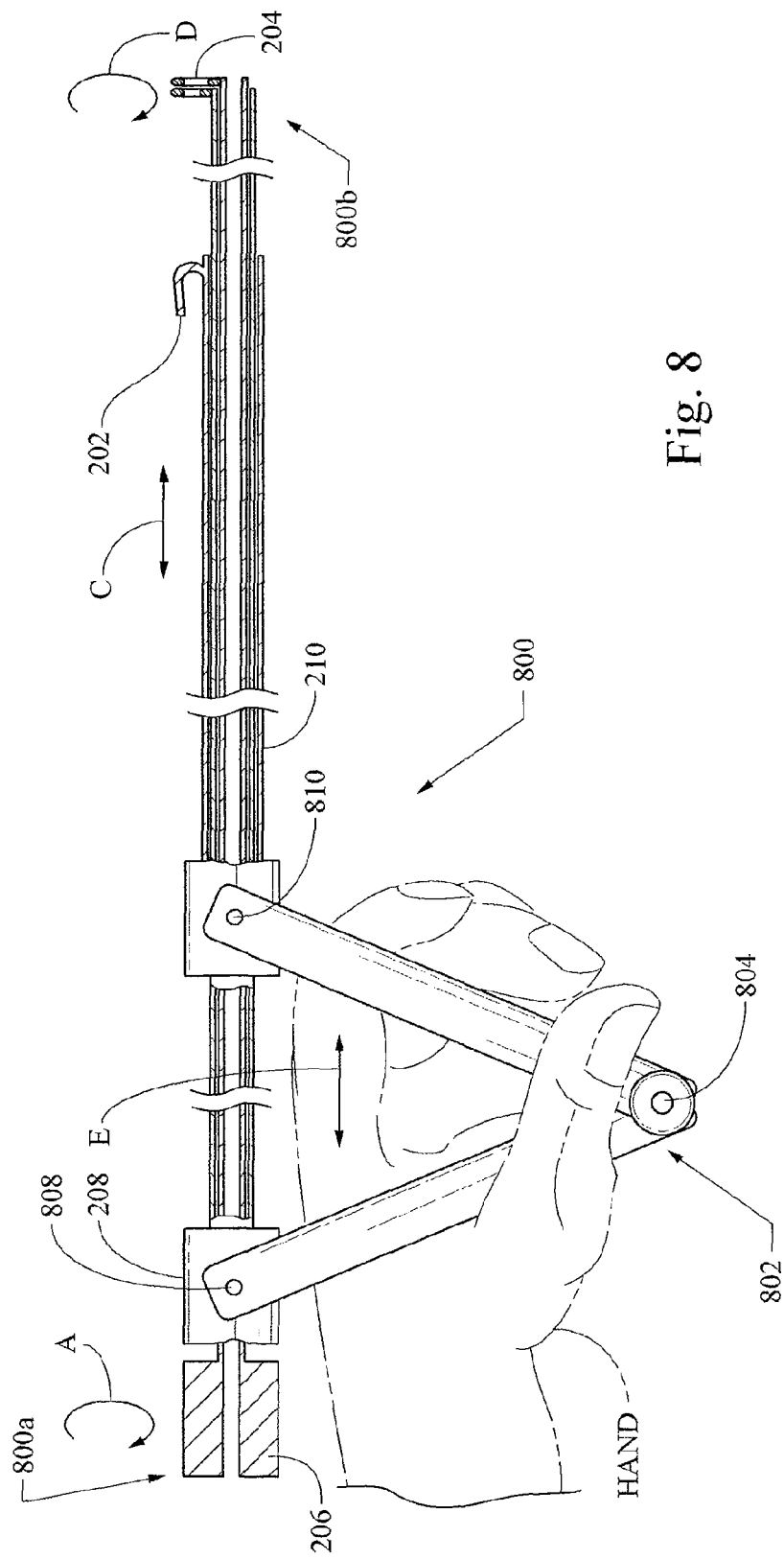
FIG. 8 illustrates an alternate sectional side view of an exemplary stent positioning device.

FIG. 8 illustrates an alternate sectional side view of the proximal portion of exemplary stent positioning device 800 having proximal portion 800*a* and distal portion 800*b*. Positioning device 800, illustrated in FIG. 8, is similar to positioning device 200 illustrated in FIG. 4, however the advancement/retraction means, illustrated as advancement/retraction member 208 in FIG. 4 further includes handle 802, illustrated in FIG. 8.

Handle 208 is able to provide precise manipulation of the stent as the stent starts to collapse down using system 800. Thus, it provides a mechanical aid to help provide more and more force so that the stent may collapse in a more controlled manner than may otherwise be available by manually sliding a push-pull system. In other words, the positioning device 800 would be used similar to that of the system 200 illustrated in FIG. 4, but after the stent begins to collapse, controlled collapsing of the stent would be further achieved by use of handle 802.

Thus, actuator 206 is disengageable from engagement member 808. Accordingly, actuator 206 is first disengaged from engagement member 808 and pulled back proximally which effectively moves hook 202 and actuation member 204 close together on the proximal side of the stent. Once the stent sutures are engaged with hook 202 and actuation member 204, actuator 206 is pushed distally which effectively moves actuation member 204 through the stent.

Thereafter, at the point where actuation member 204 starts to engage and collapse the stent, actuator 206 is right next to engagement member 808 and at that point, actuator 206 is coupled to engagement member 808. Once coupled together, handle 802 is used to start and complete the collapsing of the stent.

Accordingly, first engagement member 808 is connected to advancement/retraction member 208. Second handle engagement member 810 is connected to shaft 210. Handle 802 is compressible and expandable through pivot joint 804 in the directions of Arrow E, and it is configured for single-hand use. To use handle 802, a user places their hand around handle 802. When user compresses handle 802, first engagement member 808 and second engagement member 810 draw closer such that advancement/retraction member 208 is distally slid within shaft 210 causing actuation member 204 to move distally from hook 202 thereby causing an attached stent (not shown) to collapse. When the compressive force on handle 802 is released, pivot joint 804 causes first engagement member 808 and second engagement member 810 to spread apart thereby causing advancement/retraction member 208 to slide proximally within shaft 210 causing actuation member 204 to move proximally toward hook 202 thereby permitting an attached stent (not shown) to expand.

Alternatively, advancement/retraction member 208 may be partially advanced or retracted into any number of positions by partially compressing or uncompressing handle 802.

Other configurations for positioning devices 200, 800 and equivalents thereto are contemplated, including but not limited to, those configured with multiple hooks, actuating members, other handle configurations, and/or combinations thereof so as to easily engage and disengage a stent for deployment into, repositioning, and removal from a patient.

Additionally, it is contemplated that positioning device 200, 800 and equivalents thereto be a reusable device, such that it can be configured for use with multiple stents. Alternatively, positioning device 200, 800 and equivalents thereto may be disposable. Alternatively, positioning device 200, 800 and equivalents thereto may be retained for removal of the stent after the stent is no longer needed or desired to be dwelling within a patient. Alternatively, positioning device 200, 800 and equivalents thereto may be retained for repositioning of the stent in the event the stent needs to be moved after dwelling within a patient.

While numerous benefits of the system can be seen, including, but not limited to, the efficient deployment and removal of the stent. Additional benefits include, but are not limited to, fewer traumas to the patient. For example, current method of removal of a stent including pulling the proximal portion of the stent, which may thereby cause damage to the surrounding tissue, especially when the stent is embedded due to tissue growth or from another means. When used to remove a stent, positioning device 200, 800 and equivalents thereto bear the force, rather than the force being exerted on the surrounding tissue, thereby reducing the trauma to the surrounding tissue when the stent is removed.

From the foregoing, the discovery of a stent and system for the delivery, repositioning, and removal of a stent benefits a patient through a system that uses the inherent properties of such a stent, including foreshortening. As such, the stent can be radially constrained to reduce its diameter by applying a tensile force along its proximal and distal ends to collapse the stent permitting the efficient delivery, repositioning, and removal of the stent with less trauma to the patient.

It can be seen that the systems, apparatuses, and methods illustrated and equivalents thereof may utilize machines or other resources, such as human beings, thereby reducing the time, labor, and resources required to manufacturer or use a stent and a delivery device. Indeed, the discovery is not limited to the embodiments illustrated herein, and the principles, apparatuses, and methods illustrated herein can be applied and configured to any stent, delivery system, and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A stent comprising:
    an elongated tubular body comprising a proximal portion, a distal portion, and a lumen extending between the proximal portion and the distal portion, wherein the elongated tubular body comprises one or more wires;
    a first suture connected circumferentially about the proximal portion of the elongated tubular body, wherein the first suture is configured into a first grasping loop;
    a second suture connected circumferentially about the distal portion of the elongated tubular body;
    a third suture at least partially disposed within the lumen of the elongated tubular body and is longitudinally and laterally movable relative thereto, wherein the third suture comprises a first end that is fixedly connected to the first suture, a second end that is fixedly connected to the second suture, and an intermediate portion that is spaced away from the elongated tubular body;
    wherein the stent is configured to collapse and assume a collapsed diameter when opposite axial forces are applied to the first grasping loop and the intermediate portion of the third suture.

2. The stent of claim 1, wherein the stent is configured to expand and assume a second diameter, larger than the collapsed diameter, when the opposite axial forces are released from at least one of the first grasping loop or the third suture.

3. The stent of claim 1 further comprising a covering.

4. The stent of claim 3, wherein the covering comprises silicone.

5. The stent of claim 1, wherein the one or more wires comprise nitinol.

6. The stent of claim 1, wherein at least one of the first suture, the second suture, or the third suture comprises polytetrafluoroethylene (PTFE).

7. The stent of claim 1, wherein at least one of the first suture, the second suture, or the third suture is elastic.

8. The stent of claim 1, wherein the first grasping loop extends proximally from the stent.

9. The stent of claim 1, wherein the first grasping loop is disposed within the lumen of the stent.

10. The stent of claim 1, further comprising a second grasping loop attached to the second suture.

11. The stent of claim 10, wherein the second grasping loop extends distally from the stent.

12. The stent of claim 1, wherein the one or more wires are helically wound and woven to form the tubular body, said tubular body extending between a proximal crown and a distal crown, said first suture being woven through the proximal crown and said second suture being woven through the distal crown.

13. A stent positioning system comprising:
    a stent comprising:
        an elongated tubular body comprising a proximal portion, a distal portion, and a lumen extending between the proximal portion and the distal portion;
        a first suture connected circumferentially about the proximal portion of the elongated tubular body, wherein the first suture is configured into a first grasping loop;
        a second suture connected circumferentially about the distal portion of the elongated tubular body; and
        a third suture at least partially disposed within the lumen of the elongated tubular body and is movable relative thereto, wherein the third suture is fixedly connected to the first suture and the second suture only, and wherein the third suture is not connected directly to the elongated tubular body;
    a positioning device comprising:
        a proximal portion;
        a distal portion;
        a shaft;
        a hook disposed on an outer surface of the shaft and configured to engage the first grasping loop of the stent;
        an actuation member configurable into an open position and a closed position, wherein the actuation member is configured to engage the third suture of the stent;
        an actuator in communication with the actuation member, wherein the actuator is configured to open and close the actuation member;
        an advancement/retraction member in communication with the actuator and the actuation member, wherein the advancement/retraction member is slideably disposed within at least a portion of the shaft, wherein the advancement/retraction member is configured to axially move the actuation member in a direction proximally toward and distally from the hook;
    wherein, the stent is configured to collapse and assume a collapsed diameter when the actuation member is engaged with an intermediate portion of the third suture, wherein the hook is engaged with the first grasping loop, and further wherein the advancement/retraction member is directed axially such that the actuation member is moved distally from the hook.

14. The stent positioning system of claim 13, wherein the stent is configured to expand and assume a second diameter, larger than the collapsed diameter, when the advancement/retraction member is directed axially such that the actuation member is moved toward the hook.

15. The stent positioning system of claim 13, wherein the positioning device further comprises a handle configured to advance and retract the actuation member relative to the hook.

* * * * *